(12) United States Patent
Maschke

(10) Patent No.: US 9,149,245 B2
(45) Date of Patent: Oct. 6, 2015

(54) DEVICE AND METHOD FOR TAKING A HIGH ENERGY IMAGE

(75) Inventor: Michael Maschke, Lonnerstadt (DE)

(73) Assignee: SIEMENS AKTIENGESELLSCHAFT, München (DE)

(*) Notice: Subject to any disclaimer, the term of this patent is extended or adjusted under 35 U.S.C. 154(b) by 2642 days.

(21) Appl. No.: 10/587,671

(22) PCT Filed: Jan. 20, 2005

(86) PCT No.: PCT/EP2005/050248
§ 371 (c)(1),
(2), (4) Date: Jul. 27, 2006

(87) PCT Pub. No.: WO2005/072614
PCT Pub. Date: Aug. 11, 2005

(65) Prior Publication Data
US 2007/0160180 A1      Jul. 12, 2007

(30) Foreign Application Priority Data
Jan. 29, 2004   (DE) .......................... 10 2004 004 626

(51) Int. Cl.
*A61B 5/05*      (2006.01)
*A61B 6/00*      (2006.01)
*A61B 6/12*      (2006.01)

(52) U.S. Cl.
CPC . *A61B 6/545* (2013.01); *A61B 6/12* (2013.01); *A61B 6/504* (2013.01)

(58) Field of Classification Search
USPC .................... 600/16, 407; 607/9; 623/1.1–3.1
See application file for complete search history.

(56) References Cited

U.S. PATENT DOCUMENTS

| | | | |
|---|---|---|---|
| 5,835,561 A * | 11/1998 | Moorman et al. | 378/98 |
| 6,394,952 B1 * | 5/2002 | Anderson et al. | 600/300 |
| 6,907,104 B2 * | 6/2005 | Pronk | 378/62 |
| 2002/0013540 A1 * | 1/2002 | Jacobsen et al. | 600/585 |
| 2002/0077547 A1 | 6/2002 | Sluis | |
| 2003/0197734 A1 * | 10/2003 | Binkert et al. | 345/771 |
| 2003/0204248 A1 * | 10/2003 | Murphy | 623/1.34 |
| 2003/0230630 A1 * | 12/2003 | Whipple et al. | 235/462.01 |
| 2004/0267297 A1 * | 12/2004 | Malackowski | 606/167 |
| 2005/0197536 A1 * | 9/2005 | Banik et al. | 600/179 |

FOREIGN PATENT DOCUMENTS

| | | |
|---|---|---|
| DE | 38 17 342 A1 | 11/1989 |
| DE | 19702896 A1 | 7/1997 |
| DE | 198 09 738 A1 | 9/1999 |
| DE | 10324905 A1 | 12/2004 |
| WO | WO 97/25923 A2 | 7/1997 |
| WO | WO 02/093986 A1 | 11/2002 |
| WO | WO 03/059166 A2 | 7/2003 |

* cited by examiner

*Primary Examiner* — Joel F Brutus

(57) ABSTRACT

The invention relates to a device for taking high energy images, in particular, X-ray images, comprising an input image by means of which data for a medical auxiliary may be inputted into the device. Said medical auxiliaries are preferably stents or contrast agents which can be introduced into the body of a patient. The display unit of the device can thus be correspondingly set for the applied auxiliary.

14 Claims, 3 Drawing Sheets

DEVICE AND METHOD FOR TAKING A HIGH ENERGY IMAGE

CROSS REFERENCE TO RELATED APPLICATIONS

This application is the US National Stage of International Application No. PCT/EP2005/050248, filed Jan. 20, 2005 and claims the benefit thereof. The International Application claims the benefits of German application No. 10 2004 004 626.3 DE filed Jan. 29, 2004, both of the applications are incorporated by reference herein in their entirety.

FIELD OF INVENTION

The invention relates to a device for taking a high energy image of an object under examination into which an adjuvant can be inserted, said device comprising an imaging unit for taking the high energy image and a control unit which controls the recording of the high energy image.

The invention further relates to a method for taking a high energy image.

BACKGROUND OF THE INVENTION

A device and method of this kind are known from DE 198 09 738 A1. The device disclosed here is an x-ray diagnostic device having a control unit for preadjusting the aperture settings required for taking the image. The control unit has direct access to a data memory containing patient data and can also access an organ program memory containing default aperture setting values. The disclosed device is also able to determine the size of the organ under examination from patient-related data and set the optimum aperture value using servo motors.

The disclosed device is particularly suitable for examination of the lung in a digital pulmonary workstation.

X-ray equipment is also well-known for its use in angiography systems which are used among other things to insert devices known as stents into coronary vessels in a cardiological context. Stents are medical adjuvants generally consisting of short metal tubes with a reticulated wall structure. They can be expanded using balloon catheters. Expanding the balloon catheter inserted in a coronary vessel also causes the coronary vessel to be dilated. After removal of the balloon catheter from the coronary vessel, the expanded stents ensure that the coronary vessel remains dilated. The stents are inserted and aligned using the x-ray angiography systems.

Reliably detecting stents in angiographic examinations is a major technical challenge, particularly in radioscopy mode. As the stents are made by different manufacturers, they differ markedly in respect of material used and mechanical design, which makes it difficult to adjust the angiography system such that both the stent and the surrounding tissue are clearly discernible to medical personnel. The challenges for detecting stents will increase still further with what are known as drug eluting stents (DES), because the DES are coated with a material designed to prevent restenosis of the coronary vessel. These additional coatings make it even more difficult to detect the stents in the x-ray image. In addition, stents made of biodegradable material are being developed. Such a stent is the so-called Igaki-Tamai stent made of poly-L-lactic acid. Such stents made of biodegradable material are difficult to show with sufficient contrast in x-ray images.

SUMMARY OF THE INVENTION

Proceeding from this prior art, the object of the invention is to specify a device and a method for taking high energy images enabling adjuvants present in the object under examination to be displayed with good quality.

This object is achieved according to the invention by a device and a method having the features set forth in the independent claims. Advantageous embodiments and developments are detailed in the dependent claims.

The device for taking high energy images has a control unit to which data relating to the medical adjuvant can be fed via an input device. The control unit is then able to set operating parameters of the imaging unit according to the adjuvant data in such a way that the high energy image taken reproduces both the adjuvant disposed inside the object under examination and the adjacent area with sufficient clarity. The device therefore eliminates the laborious process of searching for optimum settings for the imaging unit. Instead, knowledge already available about the nature of the imaging object is used to set the imaging unit accordingly.

In a preferred embodiment, the device is a device for taking a high energy image of a patient's body region into which a medical adjuvant such as a stent or contrast agent has been inserted. By entering the data relating to said medical adjuvant, the imaging unit can be adjusted by the control unit in such a way that the high energy images clearly show both the medical adjuvant and the adjacent regions of the body of the patient being examined.

In a further preferred embodiment, the device is equipped with a scanner with which adjuvant data can be read in from the adjuvant's packaging. The advantage of this embodiment is that data transfer is automatic, which eliminates human error when entering data.

In another preferred embodiment, the data relating to the adjuvant is stored in a memory which the control unit can access. The corresponding data record is then selected by entering a code identifying the adjuvant and the associated data record. With this embodiment it is therefore unnecessary to re-input the data record required for setting the imaging unit each time, thereby reducing the susceptibility to error.

In one embodiment it is additionally provided to combine data relating to the adjuvant with the data of the object under examination and to derive manipulated variables which are influenced both by the patient data and by the adjuvant data.

In response to a user input, the device can preferably be placed in an operating condition in which the device takes the adjuvant data into account for adjusting the imaging unit. Such an embodiment of the device facilitates user guidance, as the new operating condition must be deliberately selected by the user in cognizance of the particular details.

BRIEF DESCRIPTION OF THE DRAWINGS

Further features and advantages of the invention will emerge from the following description in which exemplary embodiments of the invention are explained in detail with reference to the accompanying drawings in which.

DETAILED DESCRIPTION OF INVENTION

Figure 1:
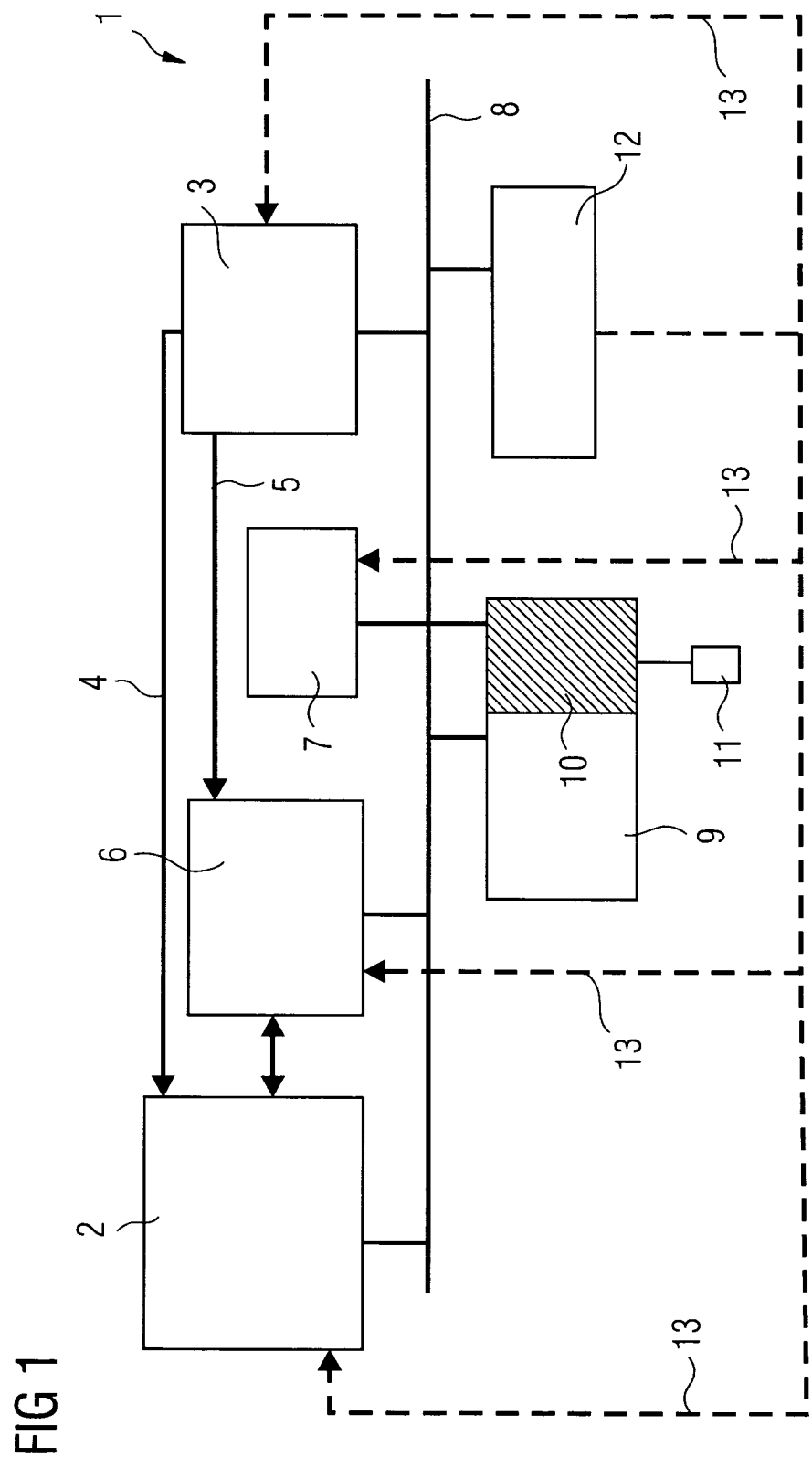
FIG. 1 shows a block diagram of an x-ray system set up to display medical adjuvants.

FIG. 1 shows an x-ray system 1 having a radiation source 2. The radiation source 2 comprises, for example, a high voltage generator and an x-ray emitter with different coiled filaments, beam apertures and various radiation filters. The radiation source 2 sends x-radiation (not shown in FIG. 1) to an x-ray detector 3 which is, for example, a flat-panel detector with additional dose measurement. The recording of the x-ray image is influenced using control data 4 on the part of the x-ray detector 3. In particular, after the start of recording, the radiation characteristics of the radiation source 2 are re-adjusted as a function of the x-radiation received by the x-ray detector 3, as the weight or size of a patient is only to a limited extent a measure of the x-radiation to be expected. Therefore, at the start of recording, an initial setting is generally used and re-adjusted as recording proceeds.

The taking of the x-ray image causes image data 5 to be generated in the x-ray detector 3 and this data is transferred to an image processing unit 6. The image processing unit 6 can contain both arithmetic elements for pre- and post-processing of the image data 5 and data or image memories.

The x-ray system 1 is controlled by means of a system controller 7 which exchanges data with the radiation source 2, the x-ray detector 3 and the image processing unit 6 via a data bus 8.

To the data bus 8 there is additionally connected a display unit 9 which forms a functional entity with the input device 10. The display unit can be a monitor, for example. The input device is typically a keyboard or control panel. To the input device 10 there is connected a scanner 11 with which an identification code indicated on the packaging of a stent or contrast agent can be scanned in. Depending on the identification code scanned in, an associated set of system parameters can be selected by the system controller 7 from a database 12 likewise connected to the data bus 8 and transferred to the radiation source 2, the image processing unit 6, the x-ray generator 3 or the system controller 7. This is indicated by dashed lines 13 in FIG. 1.

It should be noted that the identification code of the particular stent or contrast agent can also be entered manually via the input device 10. It is also possible for the relevant identification code to be obtained from an electronic patient file via a network interface.

A wide variety of data concerning the stent present or contrast agent used can be stored in the database 12. For stents, such data could include the manufacturer ("Medtronic"), the name ("S670"), the type ("slotted tube"), the length ("9/12/15/18/24/30 mm"), the diameter ("3.0/3.5/4.0 mm"), the thickness of the individual struts ("0.128 mm-0.154 mm"), the profile ("1.1 mm"), the surface area ("17-23%"), the foreshortening ("3%") and other data. Optimum parameter values of the x-ray system 1 can be assigned to the stored characteristics for the stents or contrast agent used. Said parameter values relate, for example, to the high voltage used, the current, the focus used, the aperture setting, the recording time, the absorbers used in the radiation source 2 as well as other parameters of the image processing unit 6.

Figure 2:
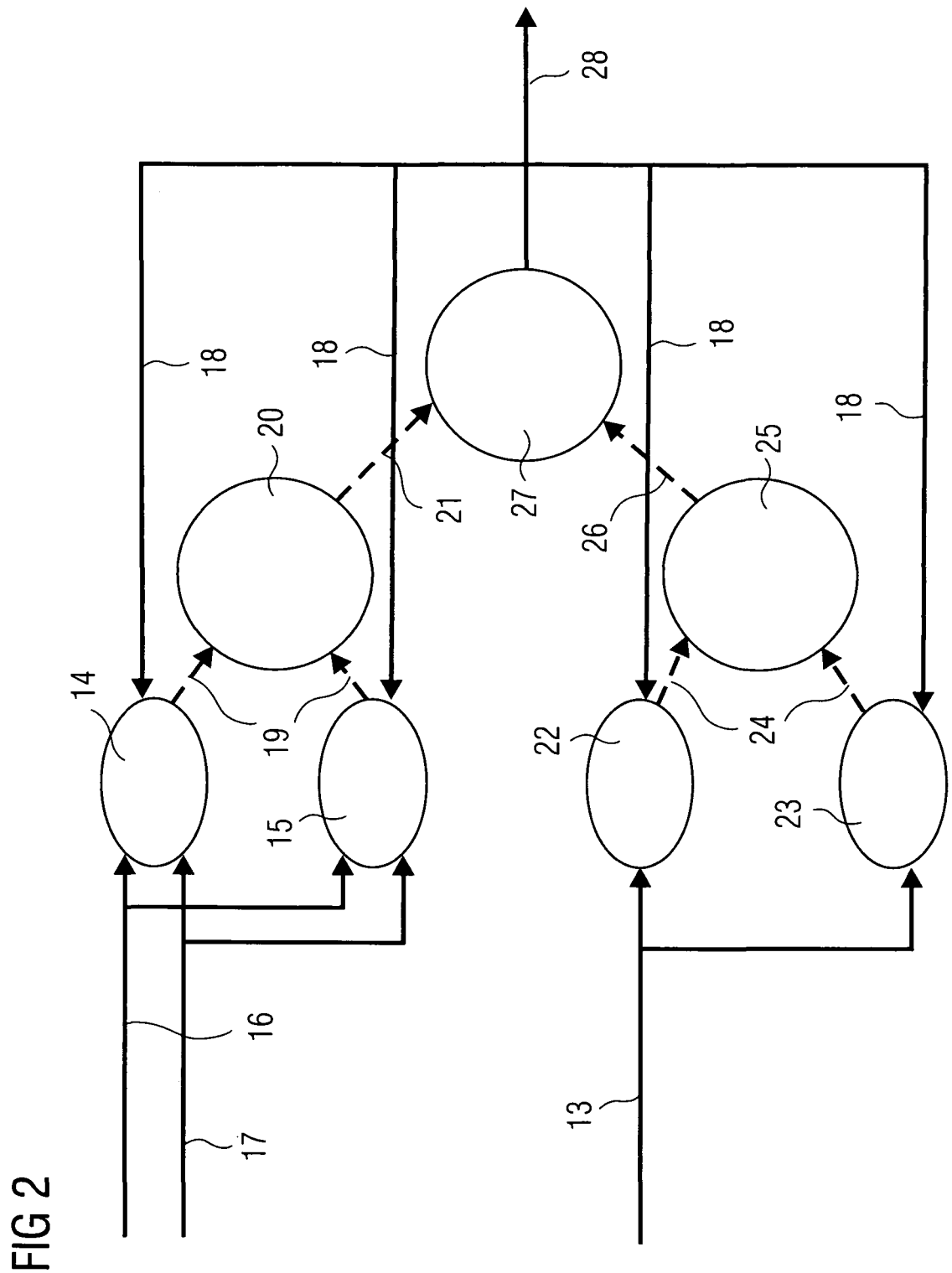
FIG. 2 shows a block diagram illustrating the control of the x-ray system according to FIG. 1.

It is additionally possible, as shown in FIG. 2, to combine the parameter values stored in the database 12 for the x-ray system 1 with parameters which are assigned to different types of patients.

According to FIG. 2, system setpoint values 16 and patient data 17 as well as actual system values 18 are applied to a dose control circuit 14 and image quality control circuit 15. The resulting manipulated variables 19 are combined in a combining unit 20 to form a common manipulated variable 21, the combining in said combining unit 20 being accomplished using lookup tables, characteristic curves or neural networks.

The system parameters 13 which are assigned to the adjuvants present, stents or contrast agents, are applied to another dose control circuit 22 and another image quality control circuit 23. The dose control circuit 22 and image quality control circuit 23 produce manipulated variables 24 which are combined in a combining unit 25 to form a common manipulated variable 26. Like the combining of the manipulated variables 19 in the combining unit 20, the combining of the manipulated variables 24 can take place via lookup tables, characteristic curves or neural networks. The manipulated variables 21 and 26 are combined in a combining unit 27 to form a manipulated variable 28. Into the manipulated variable 28 therefore go the values of the system parameters 13, the system setpoint values 16 and the patient data 17. As the patient data 17 and the employed adjuvants to be imaged are known to the x-ray system 1, the x-ray system 1 can be set such that both the adjuvant used, i.e. a stent or contrast agent, and the adjacent tissue of the patient under examination are clearly discernible by the physician on the x-ray image produced.

Note that in some circumstances a plurality of system parameters 13 must be combined for imaging a plurality of stents. This can be done by prioritizing or weighting.

The patient data 17 can be complex data records containing not only the patient's thickness but also his height, weight and girth. In addition, the patient data 17 can include typical or specific organ values.

Figure 3:
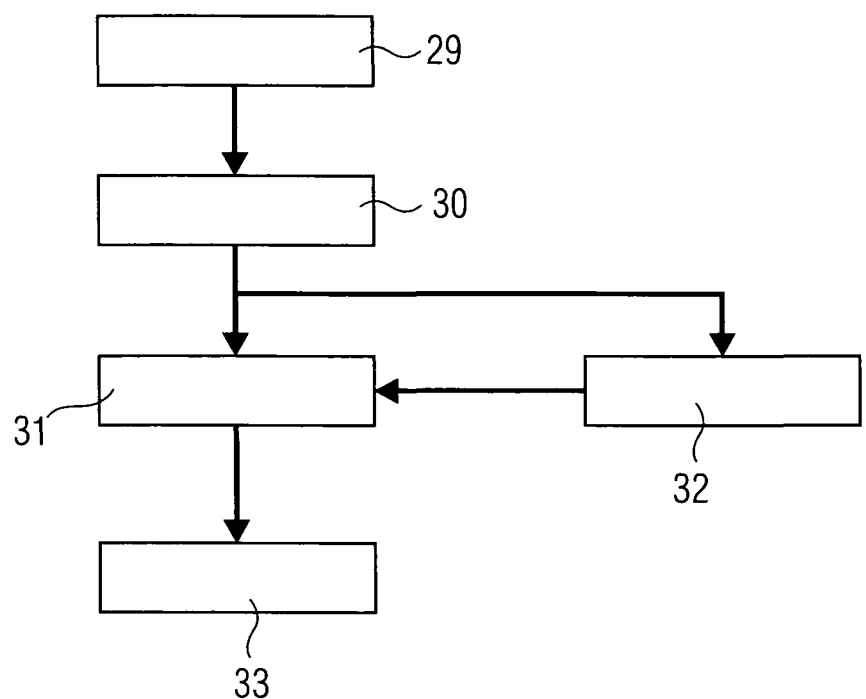
FIG. 3 shows a flowchart of a method for recording medical adjuvants and adjacent tissue.

The x-ray system 1 is typically operated as shown in FIG. 3. First patient data is entered 29. This can be done manually by the user. However, the data fed in during entry 29 can also be scanned in or transferred via a medical data network using relevant formats, e.g. the DICOM format. This is followed by inputting 30 of the identification code of the medical adjuvant used. For example, the stent identification can be scanned in from the packaging of the stent using a barcode reader. It is additionally possible to input the stent identification manually to the x-ray system 1 via an input device 10. Another possibility is to transfer the stent identification from an electronic patient file.

Then an angiographic examination 31, for example, is carried out. Optionally an optimized operating condition of the x-ray system 1 for recording the medical adjuvant can be activated by an activation process 32. When the angiographic examination 31 has been carried out, the x-ray images obtained during the angiographic examination 31 are stored 33.

Using the x-ray system 1, medical adjuvants such as stents, contrast agents, catheters or heart pacemaker electrodes together with the adjacent tissue can be displayed with high contrast. This can be implemented irrespective of the type and nature of the medical adjuvant used. The x-ray system 1 is equipped with the necessary intelligence to produce both sharp and contrasty images of the area of interest of the patient under examination that are adapted to suit the medical situation.

In conclusion, it should be pointed out that the use of an x-ray system 1 of the type described here is not limited to cardiological purposes. Rather the principles described here are also transferable to other types of x-ray systems.

The invention claimed is:

1. A medical device for taking a high energy image of an object under a medical examination into which an adjuvant is insertable, comprising:
   an x-ray imaging unit for taking a high energy x-ray image of the adjuvant inserted within the object; and
   a control unit which controls the taking of the high energy image, the control unit supplied with an identification code of the adjuvant via an input device and coupled to set operating parameters of the image unit according to the identification code to control contrast between the adjuvant and an adjacent region of the object in the high energy image.

2. The medical device according to claim 1, wherein the control unit combines the operating parameters associated with the identification code with data concerning the object under the medical examination.

3. The medical device according to claim 1, wherein the operating parameters are stored in a memory that is accessible by the control unit.

4. The medical device according to claim 1, wherein the input device is a scanner.

5. The medical device according to claim 4, wherein the scanner is a barcode reader.

6. The medical device according to claim 1, wherein the medical device has an operating condition that displays the adjuvant.

7. The medical device according to claim 1, wherein a stent and an adjacent region within the object are displayed via the imaging unit.

8. The medical device according to claim 1, wherein a contrast agent concentration in the object is displayed via the imaging unit.

9. The medical device according to claim 1, wherein the object is a patient.

10. A method for taking a high energy image of an object under medical examination containing a medical adjuvant, comprising:
   controlling the taking of the high energy image by an imaging unit via a control unit;
   inputting an identification code of the medical adjuvant into the control unit;
   setting operating parameters of the imaging unit via the control unit according to the identification code; and
   taking a high energy image of the adjuvant inserted and a region of the object with the imaging unit wherein the identification code is used by the control unit to control contrast between the adjuvant and the region of the object in the high energy image.

11. The method according to claim 10, wherein the operating parameters associated with the identification code are combined in the control unit with data concerning the object under medical examination.

12. The method according to claim 10, further comprising displaying a stent and an adjacent region within the object in an x-ray image taken by the imaging unit.

13. The method according to claim 12, further comprising displaying a contrast agent concentration within the object in the x-ray image.

14. The method according to claim 10, wherein the object is a patient.

* * * * *